US010137251B2

(12) United States Patent
Holtwick et al.

(10) Patent No.: US 10,137,251 B2
(45) Date of Patent: Nov. 27, 2018

(54) ASSEMBLY FOR A DRUG DELIVERY DEVICE AND DRUG DELIVERY DEVICE

(71) Applicant: SANOFI-AVENTIS DEUTSCHLAND GMBH, Frankfurt am Main (DE)

(72) Inventors: Marc Holtwick, Frankfurt am Main (DE); Michael Jugl, Frankfurt am Main (DE); Axel Teucher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 62 days.

(21) Appl. No.: 14/786,805

(22) PCT Filed: May 13, 2014

(86) PCT No.: PCT/EP2014/059689
§ 371 (c)(1),
(2) Date: Oct. 23, 2015

(87) PCT Pub. No.: WO2014/191189
PCT Pub. Date: Dec. 4, 2014

(65) Prior Publication Data

US 2016/0067416 A1 Mar. 10, 2016

(30) Foreign Application Priority Data

May 27, 2013 (EP) .................................... 13169308

(51) Int. Cl.
*A61M 5/315* (2006.01)
*A61M 5/20* (2006.01)
*A61M 5/31* (2006.01)

(52) U.S. Cl.
CPC .......... *A61M 5/31545* (2013.01); *A61M 5/20* (2013.01); *A61M 5/31511* (2013.01);
(Continued)

(58) Field of Classification Search
CPC ................ A61M 5/31545; A61M 5/20; A61M 5/31511; A61M 5/31533; A61M 5/31576;
(Continued)

(56) References Cited

U.S. PATENT DOCUMENTS 533,575 A 2/1895 Wilkens
5,226,895 A 7/1993 Harris
(Continued)

FOREIGN PATENT DOCUMENTS

EP 0937471 8/1999
EP 0937476 8/1999
(Continued)

OTHER PUBLICATIONS

Torsion spring: definition of torsion spring from Lee Spring, retrieved from http://www.leespring.com/int_learn_torsion.asp on Oct. 2, 2017.*
(Continued)

*Primary Examiner* — Andrew Gilbert
*Assistant Examiner* — Dung Ulsh
(74) *Attorney, Agent, or Firm* — Fish & Richardson P.C.

(57) ABSTRACT

An assembly for a drug delivery device is provided, the assembly having a compression spring, wherein the compression spring is compressed during the setting of a dose of a drug. The assembly further comprises a sleeve member, wherein the compression spring is in direct contact with the sleeve member and wherein the compression spring and the sleeve member are configured such that a relaxation of the compression spring effects a rotational and an axial movement of the sleeve member in a proximal direction, thereby causing a dispensing of a dose from the drug delivery device.

8 Claims, 1 Drawing Sheet

(52) U.S. Cl.
CPC .... *A61M 5/31553* (2013.01); *A61M 5/31576* (2013.01); *A61M 5/31583* (2013.01); *A61M 5/31563* (2013.01); *A61M 2005/202* (2013.01); *A61M 2005/3126* (2013.01)

(58) Field of Classification Search
CPC .......... A61M 5/31583; A61M 5/31563; A61M 2005/202; A61M 2005/3126
See application file for complete search history.

(56) References Cited

U.S. PATENT DOCUMENTS 5,279,586 A 1/1994 Balkwill
5,304,152 A 4/1994 Sams
5,320,609 A 6/1994 Haber et al.
5,383,865 A 1/1995 Michel
5,480,387 A 1/1996 Gabriel et al.
5,505,704 A 4/1996 Pawelka et al.
5,582,598 A 12/1996 Chanoch
5,626,566 A 5/1997 Petersen et al.
5,674,204 A 10/1997 Chanoch
5,688,251 A 11/1997 Chanoch
5,921,966 A 7/1999 Bendek et al.
5,961,495 A 10/1999 Walters et al.
6,004,297 A 12/1999 Steenfeldt-Jensen et al.
6,193,698 B1 2/2001 Kirchhofer et al.
6,221,046 B1 4/2001 Burroughs et al.
6,235,004 B1 5/2001 Steenfeldt-Jensen et al.
6,248,095 B1 6/2001 Giambattista et al.
6,899,698 B2 5/2005 Sams
6,936,032 B1 8/2005 Bush, Jr. et al.
7,241,278 B2 7/2007 Moller
7,618,393 B2* 11/2009 Bingham ................ A61M 5/30 604/131
7,686,786 B2* 3/2010 Moller .............. A61M 5/14566 604/134
9,138,542 B2* 9/2015 Smith ..................... A61M 5/20
2001/0005781 A1* 6/2001 Bergens .............. A61M 5/2033 604/208
2002/0052578 A1* 5/2002 Moller .................... A61M 5/24 604/208
2002/0120235 A1 8/2002 Enggaard
2003/0050609 A1 3/2003 Sams
2004/0059299 A1 3/2004 Moller
2004/0210199 A1 10/2004 Atterbury et al.
2004/0267207 A1 12/2004 Veasey et al.
2005/0113765 A1 5/2005 Veasey et al.
2006/0153693 A1 7/2006 Fiechter et al.
2007/0100288 A1* 5/2007 Bozeman ................ A61M 5/20 604/181
2008/0287883 A1* 11/2008 Radmer ............ A61M 5/31551 604/211
2008/0306446 A1* 12/2008 Markussen ............. A61M 5/20 604/139
2009/0012479 A1* 1/2009 Moller .................... A61M 5/20 604/211
2009/0048561 A1* 2/2009 Burren ............. A61M 5/31553 604/135
2009/0247951 A1* 10/2009 Kohlbrenner ........... A61M 5/20 604/134
2009/0275914 A1* 11/2009 Harms .................... A61M 5/24 604/506
2009/0275916 A1 11/2009 Harms et al.
2010/0114025 A1 5/2010 Moller
2010/0312196 A1* 12/2010 Hirschel ................. A61M 5/20 604/207
2010/0324492 A1* 12/2010 Peruzzo ............ A61M 5/31511 604/198
2010/0324493 A1* 12/2010 Plumptre .......... A61M 5/31541 604/207
2011/0046565 A1* 2/2011 Radmer .................. A61M 5/20 604/211
2011/0257604 A1* 10/2011 Banik ................... A61M 5/484 604/209
2012/0136315 A1* 5/2012 Wieselblad ............. A61M 5/20 604/189
2012/0209208 A1* 8/2012 Stefanski ................ A61M 5/20 604/189
2012/0232517 A1* 9/2012 Saiki ................. A61M 5/31551 604/500
2013/0197479 A1* 8/2013 Butler ............... A61M 5/31525 604/506
2013/0204193 A1* 8/2013 Holmqvist ............. A61M 5/20 604/189
2013/0296802 A1* 11/2013 Moore .................... A61M 5/24 604/246

FOREIGN PATENT DOCUMENTS

| | | |
|---|---|---|
| JP | 2010/521275 | 6/2010 |
| WO | 99/38554 | 8/1999 |
| WO | 01/10484 | 2/2001 |
| WO | 2008/037801 | 4/2008 |
| WO | WO 2008/116766 | 10/2008 |
| WO | 2011/060786 | 5/2011 |
| WO | 2012/140097 | 10/2012 |

OTHER PUBLICATIONS

International Search Report for Int. App. No. PCT/EP2014/059689, completed Jun. 24, 2014.

* cited by examiner

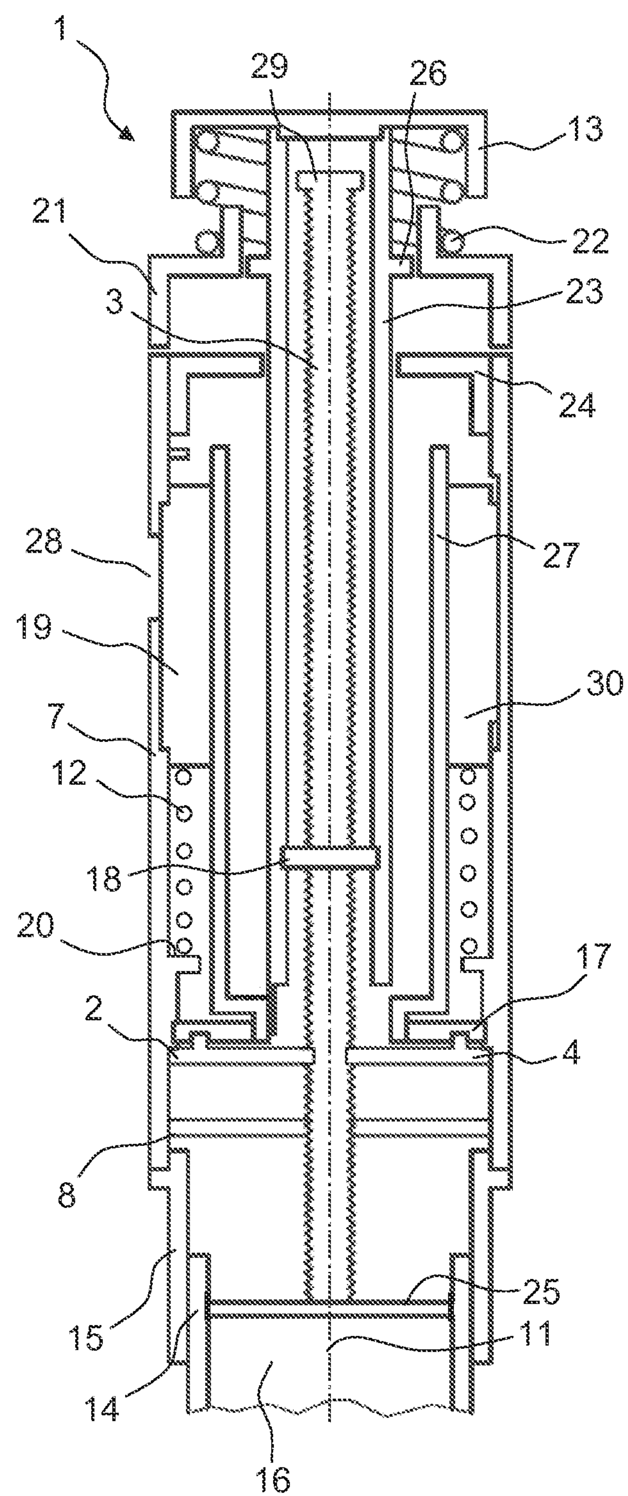
1
29
26
13
21
22
3
23
24
28
27
19
30
7
12
18
20
17
2
4
8
25
15
11
14
16

ASSEMBLY FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. § 371 of International Application No. PCT/EP2014/059689 filed May 13, 2014, which claims priority to European Patent Application No. 13169308.7 filed May 27, 2013. The entire disclosure contents of these applications are herewith incorporated by reference into the present application.

TECHNICAL FIELD

The present disclosure relates to an assembly for a drug delivery device. In particular, the disclosure relates to pen-type drug delivery devices.

BACKGROUND

Pen-type drug delivery devices are used for injections by persons without formal medical training. This is increasingly common for self-treatment among patients having diabetes or the like. Such self-treatment enables patients to effectively manage their disease. Pen-type drug delivery devices usually comprise a housing in which a drive mechanism is located. Some kinds of drug delivery devices also comprise a compartment to accommodate a cartridge in which the drug is contained. By means of the drive mechanism, a piston in the cartridge is displaced such that the drug accommodated therein is dispensed through a needle.

Prior to injection, the required dose of a drug is set by means of a dose setting mechanism. Common designs of dose setting mechanisms comprise a number of tubular or sleeve-like elements such as a dose dial sleeve, a dose indicating sleeve, a drive sleeve or a ratchet sleeve. Such sleeves are often accommodated within and connected to each other.

Some devices may comprise a spring member, wherein energy may be stored in the spring member during the setting of a dose. This energy may be released during the dispensing of a dose.

Document US 2010/0114025 A1 describes a drug delivery device comprising a spring member.

SUMMARY

It is an object of the present invention to provide an assembly for a drug delivery device having improved properties.

According to one aspect of the invention, an assembly for a drug delivery device is provided, comprising a compression spring, wherein the compression spring is compressed during the setting of a dose of a drug. The assembly further comprises a sleeve member, wherein the compression spring is in direct contact with the sleeve member and wherein the compression spring and the sleeve member are configured such that a relaxation of the compression spring effects a rotational and an axial movement of the sleeve member in a proximal direction. Thereby, a dispensing of a dose from the drug delivery device is caused. The proximal direction may be a direction away from the dispensing end of the device.

The compression spring may be an element which may be deformed, in particular compressed, in order to store energy. This energy may be released when the compression spring is allowed to relax. Thereby, the compression spring may be configured to drive another component of the assembly.

The advantage of the use of a compression spring is that the insertion of the compression spring into the assembly may be simple. In particular, the compression spring just needs to be axially inserted into the assembly. In particular, there is no need to torsionally fix the compression spring to any other parts of the drive assembly. The compression spring may be arranged between two bearing surfaces without being fixedly coupled to any component of the assembly. The rotational position of the compression spring is not relevant. Furthermore, a pre-tensioning of the compression spring may be easy, since the compression spring just needs to be compressed during the assembly. For example, the distance between the bearing surfaces may be smaller than the axial extension of the compression spring in an uncompressed state. Thereby, the compression spring may be pre-tensioned automatically during the assembly. If the compression spring is used in a reusable drug delivery device, the resetting of the device may be simple.

The sleeve member may be rotated during the setting of a dose by a user. A rotation of the sleeve member may cause a compression of the compression spring. The sleeve member may be, for example, an indicator which indicates an amount of a set dose to a user.

The assembly may comprise a dose setting member which is configured to be rotated in a dose setting direction in order to set a dose. The sleeve member may be rotated when a user rotates the dose setting member. Preferably, the sleeve member may perform a combined rotational and axial movement in a distal direction during the setting of a dose. The distal direction may be a direction towards the dispensing end of the device. During the cancelling of a dose, the sleeve member may perform a combined rotational and axial movement in a proximal direction. During the cancelling of a dose, a relaxation of the compression spring may be allowed.

According to one embodiment, the assembly comprises an actuator which is configured to be operated by a user in order to dispense a dose. The actuator may be a button. In particular, the actuator may be compressed by a user. The compression spring may be enabled to relax when the actuator is operated.

The compression spring may be a coil spring. The compression spring may exert a force on the sleeve member. The force may be directed in the proximal direction. When the device is actuated by a user and the compression spring is enabled to relax, the compression spring may cause a movement of the sleeve member.

The assembly may comprise a housing. The housing may comprise a bearing surface. In particular, the housing may comprise a protrusion, wherein the bearing surface is located at the protrusion. The bearing surface may be directed towards a proximal end of the device. The proximal end of the device may be an end which is furthest away from the dispensing end of the device. The compression spring may be arranged between the bearing surface of the housing and the sleeve member. In one embodiment, a thrust washer may be arranged between the bearing surface and the compression spring and between the sleeve member and the compression spring. Thereby, abrasion of the components of the assembly may be inhibited, in particular when the housing and the sleeve member comprise a plastic material and the compression spring comprises a metal material.

According to one embodiment, the sleeve member comprises a thread. The sleeve member may be in an engagement with the housing by means of the thread. In particular, the sleeve member may be in engagement with the housing such that a rotation of the sleeve member causes an axial movement of the sleeve member with respect to the housing. In particular, when the sleeve member is rotated in a dose setting direction, the sleeve member may be moved in a distal direction. Thereby, the sleeve member compresses the compression spring. The dose setting direction may be, for example, a clockwise direction. During the dispensing of the dose or during the cancelling of a dose, the sleeve member may be rotated in a dose dispensing direction. Thereby, the sleeve member may be moved towards the proximal end of the device. The sleeve member may be moved towards a proximal end of the device until it abuts a stop feature.

According to one embodiment, the assembly comprises a piston rod. The relaxation of the compression spring may cause the piston rod to move in a distal direction.

According to one embodiment, the assembly comprises a drive element. The drive element may be configured to cause a movement of the piston rod in a distal direction.

The drive element may be engaged with the piston rod. For example, the drive element may comprise splines, which are engaged with corresponding grooves of the piston rod. The grooves may extend along the entire length of the piston rod. In particular, the drive element may be axially moveable with respect to the piston rod. Furthermore, the drive element may be rotationally fixed with respect to the piston rod.

According to one embodiment, the assembly comprises a rotation member. The sleeve member may be rotationally fixed, but axially moveable with respect to the rotation member. For example, the sleeve member may comprise splines which engage with corresponding grooves of the rotation member. The sleeve member may be arranged concentrically around the rotation member. The rotation member may be rotated during the setting and during the dispensing of a dose. During the setting of a dose, the rotation member may be rotated in a dose setting direction, for example in a clockwise direction. During the dispensing of a dose, the rotation member may be rotated in a dose dispensing direction, for example an anticlockwise direction.

According to one embodiment, a rotation of the rotation member during the setting of a dose causes the sleeve member to rotate and axially move in a distal direction, such that the compression spring is compressed. The rotation member may be rotated by rotating the dose setting member. In particular, a rotation of the dose setting member in the dose setting direction may cause a rotation of the rotation member in the dose setting direction.

According to one embodiment, the assembly may comprise a drive shaft. The drive shaft may be coupled to the dose setting member by means of splines, which engage with corresponding grooves of the dose setting member. The rotation member may be coupled to the dose setting member by means of the drive shaft. During the dispensing of a dose, the drive shaft may be disengaged from the dose setting member.

According to one embodiment, the assembly may comprise a locking member. The locking member may be fixed with respect to the housing during the setting of a dose. In particular, the locking member and the housing may comprise corresponding engagement means. The corresponding engagement means may be engaged during the setting of a dose. The rotation member may be coupled to the locking member. The locking member may be configured to inhibit an unintended rotation of the rotation member in a dose dispensing direction during the setting of a dose. Thereby, the locking member may inhibit a relaxation of the compression spring. For this purpose, the rotation member may comprise a ratchet mechanism. The rotation member may be coupled to the locking member by means of the ratchet mechanism. The ratchet mechanism may comprise a ratchet arm. The ratchet arm may be engaged with the locking member such that an unintended rotation of the rotation member in a dose dispensing direction may be inhibited. The ratchet mechanism may allow a rotation of the rotation member in a dose setting direction with respect to the locking member.

When the actuator is actuated, the rotation member moves the locking member out of its engagement with the housing. Furthermore, a rotation of the rotation member may cause a rotation of the locking member during the dispensing of a dose.

When the actuator is actuated, the locking member may allow a rotation of the rotation member in the dose dispensing direction. In particular, the locking member may be disengaged from the housing during the dispensing of a dose. Thereby, a relaxation of the compression spring is allowed. In particular, when the actuator is actuated, the compression spring causes a rotation of the sleeve member. The sleeve member in turn rotates the rotation member due to the engagement of the sleeve member and the rotation member.

The drive element may be fixedly coupled to the locking member such that the drive element may be fixed with respect to the housing by means of the locking member at least during the setting of a dose. The drive element and the locking member may be fixed with respect to each other such that movement of the locking member causes a corresponding movement of the drive element. In particular, a rotation of the rotation member during the dispensing of a dose may cause a corresponding rotation of the drive element. Thereby, a rotation of the piston rod may be caused.

During the dispensing of a dose, the locking member may rotate with respect to the housing. Thereby, the drive element may rotate with respect to the housing during the dispensing of a dose. Thereby, the drive element may effect a movement of the piston rod. In order to enable a rotation of the locking member, the locking member has to be released from its engagement with the housing. For example, the locking member has to be axially moved with respect to the housing in order to enable a rotation of the locking member. For example, the locking member may be moved in a distal direction in order to enable a rotation of the locking member.

According to one embodiment, the assembly comprises a guiding element. The guiding element may be fixed with respect to the housing. Furthermore, the guiding element may be in engagement with the piston rod. The guiding element may influence the movement of the piston rod. When the piston rod is rotated, for example, due to a rotation of the drive element, the piston rod is caused to axially move as a result of its cooperation with the guiding element. In particular, the piston rod is rotated by the drive element during the setting of a dose such that it is moved in a distal direction. Thereby, a dose may be dispensed from the drug delivery device. According to one embodiment, the guiding element may be in threaded engagement with the piston rod.

According to a preferred embodiment, the assembly is configured such that a rotation of the drive element causes a rotational movement of the piston rod. In particular, a rotation of the drive element causes a combined axial and rotational movement of the piston rod. In particular, when the piston rod is rotated by the drive element, the piston rod rotates through the guiding element. During the setting of a dose, the drive element may be fixed with respect to the housing.

According to a further aspect of the invention, a drug delivery device is provided. The drug delivery device comprises an assembly which may be configured as previously described.

The drug delivery device may be an injection device, in particular a pen-type device. The drug delivery device may be suited to deliver a dose of a drug to a user. A dose may be delivered by depressing the actuator. The drug delivery device may be a variable dose device such that a user can select the size of a dose. In particular, a user may select the size of a dose by rotating the dose setting member. The drug delivery device may be configured for multiple dose applications. The drug may be delivered to a user by means of a needle. The device may be delivered to a user in a fully assembled condition ready for use. In particular, the device may be prefilled. The drug delivery device may be a disposable device. The term "disposable" means that the drug delivery device cannot be reused after an available amount of a drug has been delivered from the drug delivery device. Alternatively, the drug delivery device may be a reusable device. The drug delivery device may be configured to deliver a liquid drug. The drug may be, for example, insulin.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N- palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω- carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

BRIEF DESCRIPTION OF THE FIGURES

FIG. 1 shows a drug delivery device.

FIG. 1 shows a drug delivery device 1 comprising an assembly 2. In particular, FIG. 1 shows the drug delivery device 1 in a state when it is not being operated, i. e. when no dose is being delivered from the device.

DETAILED DESCRIPTION

The assembly 2 comprises a piston rod 3, which is configured to be moved in a distal direction in order to dispense a dose of a drug. In particular, the piston rod 3 is configured to move a piston 16 which is arranged in a cartridge 14 towards the dispensing end of the drug delivery device 1. In particular, the piston rod 3 comprises a bearing 25, wherein the bearing 25 is in contact with the piston 16. The cartridge is arranged in a cartridge holder 15, which is connected to a housing 7. The piston rod 3 is configured as a lead screw.

In order to set a dose, the assembly 2 comprises a dose setting member 21. The dose setting member 21 may be rotated by a user. In particular, the dose setting member 21 is axially fixed but rotationally moveable with respect to the housing 7. In particular, the length of the drug delivery device 1 does not change during a rotation of the dose setting member 21. The assembly 2 further comprises a drive shaft 23. By rotating the dose setting member 21, the drive shaft 23 is also rotated. In particular, the drive shaft 23 may be rotationally fixed with respect to the dose setting member 21 during the setting of a dose by means of splines 26. The splines 26 may engage with corresponding grooves (not shown) of the dose setting member 21.

The assembly 2 furthermore comprises a rotation member 27. The rotation member 27 is configured as a sleeve. The rotation member 27 is arranged concentrically around the drive shaft 23. The rotation member 27 may be fixed to the drive shaft 23 by a snap connection. The rotation member 27 is axially fixed with respect to the drive shaft 23. For assembly reasons, the drive shaft 23 and the rotation member 27 are designed as separate parts. In an alternative embodiment, the drive shaft 23 and the rotation member 27 may be designed as one part. Rotating the drive shaft 23 in a dose setting direction also rotates the rotation member 27. The dose setting direction may be a clockwise direction. The rotation member 27 and the drive shaft 23 are rotationally coupled. Yet, a small amount of rotational movement between the rotation member 27 and the drive shaft 23 is possible.

The assembly 2 comprises a compression spring 12. The compression spring 12 may be a coil spring. When the rotation member 27 is rotated during the setting of a dose, the compression spring 12 is compressed, such that energy is stored in the compression spring 12.

The assembly 2 further comprises an indicator 19. The indicator 19 may be a sleeve member 30, for example a number sleeve. The indicator 19 is configured to indicate the amount of a set dose to a user. For example, the amount of a set dose may be shown through a window 28 in the housing 7 of the drug delivery device 1. The indicator 19 is rotationally fixed, but axially moveable with respect to the rotation member 27. For example, the indicator 19 may comprise splines at its inner circumference which may engage in corresponding grooves of the rotation member 27. In particular, the indicator 19 is arranged concentrically around the rotation member 27. Furthermore, the indicator 19 is in threaded engagement with the housing 7. During the setting of a dose, the indicator 19 is rotated by the rotation member 27 in the dose setting direction. Thereby, the indicator 19 is forced to move in a distal direction because of its threaded engagement with the housing 7. In order to cancel a set dose, the dose setting member 21 may be rotated in a dose cancelling direction. The dose cancelling direction may be the anticlockwise direction.

The compression spring 12 is arranged between the indicator 19 and a bearing surface 20 of the housing 7. When the indicator 19 is moved in a distal direction during the setting of a dose, the compression spring 12 is compressed by the indicator 19.

The assembly 2 further comprises a locking member 17. The locking member 17 is rotationally fixed with respect to the housing 7 during the setting of a dose. For example, the locking member 17 comprises splines which engage with corresponding grooves of the housing 7. On an inner circumference of the locking member 17, a set of teeth (not shown) is arranged. The rotation member 27 is engaged with the set of teeth of the locking member 17 by means of at least one ratchet arm (not shown). In particular, the locking member 17 and the rotation member 27 are engaged such that the rotation of the rotation member 27 in a dose setting direction is allowed during the setting of a dose, and an unintended rotation of the rotation member 27 in a dose cancelling direction is inhibited. Thereby, it is inhibited that the force from the compression spring 12 rotates the rotation member 27 in a dose cancelling direction when a user releases the dose setting member 21. During the setting of a dose, the at least one ratchet arm of the rotation member 27 is moved over the teeth of the locking member 17. Thereby, an audible click may be produced with each unit set.

In order to cancel a set dose, a user rotates the dose setting member 21 in a dose cancelling direction. During the cancelling of a dose, the drive shaft 23 may rotate relative to the rotation member 27 by a short distance. Thereby, a feature, for example a protrusion of the drive shaft 23, slides over the at least one ratchet arm of the rotation member 27. Thereby, the at least one ratchet arm of the rotation member 27 is pressed in a radial inward direction. Thereby, the engagement between the rotation member 27 and the locking member 17 is temporarily released, such that the rotation member 27 may be rotated in a dose cancelling direction.

A last dose member 18 is arranged between the piston rod 3 and the drive shaft 23. The last dose member 18 may be a last dose nut. The last dose member 18 is in threaded engagement with the piston rod 3. Furthermore, the last dose member 18 is engaged with the drive shaft 23 by means of external ribs which engage in corresponding grooves inside the drive shaft 23. In particular, the last dose member 18 is rotationally fixed but axially moveable with respect to the drive shaft 23. When the drive shaft 23 rotates, for example during the setting of a dose, the last dose member 18 is rotated by the drive shaft 23. Thereby, the last dose member 18 moves along the piston rod. When a last dose is selected, the last dose member 18 abuts a stop feature 29. The stop feature 29 is arranged at a proximal end of the piston rod 3.

When the last dose member 18 abuts the stop feature 29, the further setting of a dose is inhibited. In particular, the last dose member 18 inhibits the setting of a dose which exceeds the remaining amount of drug in the cartridge 14.

In order to dispense a dose, the actuator 13 has to be actuated by a user.

When the actuator 13 is actuated, in particular moved in a distal direction, the drive shaft 23 is also moved in a distal direction. Thereby, the drive shaft 23 is disengaged from the dose setting member 21. When the drive shaft 23 is moved in a distal direction, the rotation member 27 and the locking member 17 are also moved in a distal direction together with the drive shaft 23. Thereby, the locking member 17 is disengaged from its engagement with the housing 7. In particular, the locking member 17 is allowed to rotate with respect to the housing 7 when the actuator 13 is actuated by a user. When the locking member 17 is allowed to rotate, the rotation member 27 and the indicator 19 are allowed to rotate. When the locking member 17 is enabled to rotate with respect to the housing 7, the energy which is stored in the compression spring 12 may be released. In particular, the compression spring 12 exerts a force on the indicator 19. Thereby, the indicator 19 is forced to move in a proximal direction. Due to the threaded engagement of the indicator 19 with the housing 7, an axial movement of the indicator 19 requires a rotation of the indicator 19. Accordingly, when the actuator 13 is actuated, the compression spring 12 causes the indicator 19 to rotate and axially move towards the proximal end of the device. A rotation of the indicator 19 also causes a rotation of the rotation member 27. A rotation of the rotation member 27 during the dispensing of a dose also rotates the locking member 17.

The assembly 2 comprises a drive element 4. The drive element 4 is configured as a spline nut. The drive element 4 is connected to the locking member 17. In particular, the drive element 4 is rotationally and axially fixed with respect to the locking member 17. Thereby, the drive element 4 rotates during the dispensing of a dose. Furthermore, the drive element 4 is engaged with the piston rod 3. In particular, the drive element 4 comprises splines, which are engaged with axial grooves of the piston rod 3. Thereby, the drive element 4 is rotationally fixed but axially moveable with respect to the piston rod 3.

The drive element 4 may comprise a feedback feature (not shown). For example, at the outer circumference of the drive element 4, at least one, for example two, clicker arms, may be arranged. When the drive element 4 rotates during the dispensing of a dose, the clicker arms may move over teeth in the housing 7, thereby creating an audible feedback. The feedback may indicate to a user that a dose is currently being dispensed. Accordingly, an end of the audible feedback indicates to a user that a complete dose has been dispensed.

The assembly 2 further comprises a guiding element 8. The guiding element 8 is configured as a thread nut. The guiding element 8 is in threaded engagement with the piston rod 3. The guiding element 8 is fixed with respect to the housing 7 of the drug delivery device 1. When the drive element 4 rotates during the dispensing of a dose, the piston rod 3 is also rotated. Due to the threaded engagement between the piston rod 3 and the guiding element 8, the rotation of the piston rod 3 causes the piston rod 3 to move in a distal direction. Thereby, the piston 16 is moved in a distal direction and thereby a dose is dispensed. During the dispensing of a dose, the indicator 19 is rotated back to its initial position. In particular, during the dispensing of a dose, the indicator 19 performs a combined rotational and axial movement towards a proximal end of the device, until the indicator 19 abuts a zero stop 24. The zero stop 24 is rigidly fixed to the housing 7. Alternatively, the zero stop 24 may be an integral part of the housing 7. When the indicator 19 abuts the zero stop 24, a further rotation of the rotation member 27 in a dose dispensing direction due to the force of the compression spring 12 is inhibited. Thereby, a further dispensing of a dose is inhibited.

When a user releases the actuator 13, a reset spring 22, which is arranged between the actuator and the dose setting member 21, moves the actuator back to its initial position. Thereby, the drive shaft 23 is moved in a proximal direction together with the actuator 13. Thereby, the drive shaft 23 reengages with the dose setting member 21. Furthermore, the locking member 17 reengages with the housing 7.

The invention claimed is:

1. An assembly for a drug delivery device, comprising:
- a compression spring, wherein the compression spring is compressed during a setting of a dose of a drug;
- a sleeve member,
- a rotation member, wherein the sleeve member is rotationally fixed and axially moveable with respect to the rotation member;
- a dose setting member which is configured to be rotated in a dose setting direction in order to set a dose, wherein a rotation of the dose setting member in the dose setting direction causes a rotation of the rotation member in the dose setting direction, wherein the rotation member is coupled to the dose setting member by means of a drive shaft;
- an actuator which is configured to be operated in order to dispense the dose of the drug, wherein the compression spring is enabled to relax when the actuator is operated; and
- a locking member which is configured to inhibit a rotation of the rotation member in a dose dispensing direction during the setting of the dose, thereby inhibiting a relaxation of the compression spring,
- wherein the compression spring abuts the sleeve member and wherein the compression spring and the sleeve member are configured such that the relaxation of the compression spring effects a rotational movement and an axial movement of the sleeve member in a proximal direction away from a dispensing end of the drug delivery device, thereby causing a dispensing of the dose from the drug delivery device, and wherein the assembly further comprises a housing, wherein the compression spring is arranged between a bearing surface of the housing and the sleeve member, and wherein the compression spring exerts a force on the sleeve member which is directed in the proximal direction.

2. The assembly according to claim 1, wherein the sleeve member is rotated during the setting of the dose, and wherein a rotation of the sleeve member causes a compression of the compression spring.

3. The assembly according to claim 1, wherein the compression spring is a coil spring.

4. The assembly according to claim 1, wherein the sleeve member comprises a thread, wherein the sleeve member is in engagement with the housing by means of the thread such that a rotation of the sleeve member causes an axial movement of the sleeve member with respect to the housing.

5. The assembly according to claim 1, comprising a piston rod, wherein the relaxation of the compression spring causes the piston rod to move in a distal direction.

6. The assembly according to claim 1, wherein the rotation of the rotation member during the setting of a dose causes the sleeve member to rotate and axially move in a distal direction such that the compression spring is compressed.

7. The assembly according to claim 1, wherein the locking member allows the rotation of the rotation member in the dose dispensing direction when the actuator is actuated, thereby allowing the relaxation of the compression spring.

8. A drug delivery device, comprising the assembly according to claim 1.

* * * * *